United States Patent [19]

Martel et al.

[11] 4,312,817
[45] Jan. 26, 1982

[54] IMINO DERIVATIVES

[75] Inventors: Jacques Martel, Bondy; Jean Tessier, Vincennes; André Teche, Paris, all of France

[73] Assignee: Roussel Uclaf, Paris, France

[21] Appl. No.: 212,566

[22] Filed: Dec. 3, 1980

[30] Foreign Application Priority Data

Dec. 17, 1979 [FR] France .............................. 79 390843

[51] Int. Cl.³ .......................................... C07C 121/84
[52] U.S. Cl. ................................. 260/465 D; 560/124
[58] Field of Search .................................... 260/465 D

[56] References Cited

U.S. PATENT DOCUMENTS 3,922,269 11/1975 Elliott et al. ..................... 260/347.4
4,237,163 12/1980 Roman ................................. 424/304
4,282,249 8/1981 Roman et al. ....................... 424/304

Primary Examiner—Dolph H. Torrence
Attorney, Agent, or Firm—Hammond & Littell, Weissenberger and Muserlian

[57] ABSTRACT

Novel imino derivatives of esters of 3-formyl-cyclopropane-1-carboxylic acids in their various isomeric forms and mixtures thereof of the formula

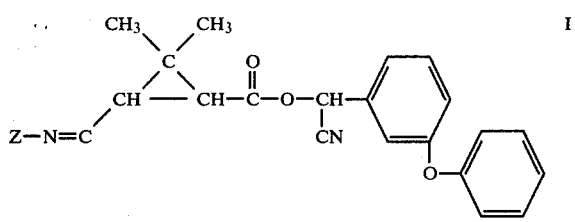

wherein Z is an organic residue of a primary amine of the formula Z-NH₂ and the acid moiety may have the cis or trans configuration and the alcohol moiety may have the R,S or RS configuration, novel intermediates therefore and a process for the preparation of the corresponding 3-substituted vinyl esters having insecticidal activity.

10 Claims, No Drawings

IMINO DERIVATIVES

STATE OF THE ART

Known process for the preparation of α-cyano-3-phenoxy-benzyl esters of cyclopropane-1-carboxylic acids are described in French Pat. No. 2,183,259, U.S. Pat. No. 3,914,279 and commonly assigned, copending U.S. Patent application Ser. No. 951,184 filed October 13, 1978 now U.S. Pat. No. 4,277,617.

OBJECTS OF THE INVENTION

It is an object of the invention to provide the novel esters of formula I and a process for their preparation and novel intermediates.

It is another object of the invention to provide a novel process for the preparation of α-cyano-3-phenoxy-benzyl esters of 3-substituted-vinyl-cyclopropane-1-carboxylic acids.

These and other objects and advantages of the invention will become obvious from the following detailed description.

THE INVENTION

The novel imino derivatives of the invention are esters of 3-formyl-cyclopropane-1-carboxylic acids in their various isomeric forms and mixtures thereof of the formula

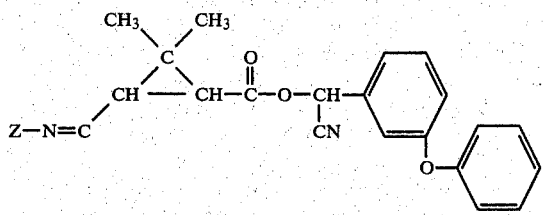

wherein Z is an organic residue of a primary amine of the formula Z-NH$_2$ and the acid moiety may have the cis or trans configuration and the alcohol moiety may have the R,S or RS configuration.

The Z substituent is derived from primary amines such as aliphatic primary amines, especially those containing 6 to 18 carbon atoms; cycloaliphatic amines of 4 to 8 carbon atoms; primary aromatic amines, especially phenyl amines optionally substituted with at least one member of the group consisting of alkyl and alkoxy of 1 to 6 carbon atoms, halogens, nitro and —SO$_3$H; optionally substituted polycyclic aromatic primary amines; and polycyclanic amines optionally of the endo or spiro type. The Z group is preferably derived from aniline.

Examples of specific preferred compounds of formula I are (RS)α-cyano-3-phenoxy-benzyl 1R, cis 2,2-dimethyl-3-(phenyliminomethyl)-cyclopropane-1-carboxylate, (S)α-cyano-3-phenoxy-benzyl 1R, cis 2,2-dimethyl-3-(phenyliminomethyl)-cyclopropane-1-carboxylate, (RS)α-cyano-3-phenoxy-benzyl 1R, trans 2,2-dimethyl-3-(phenyliminomethyl)-cyclopropane-1-carboxylate and (S)α-cyano-3-phenoxy-benzyl 1R, trans 2,2-dimethyl-3-(phenyliminomethyl)-cyclopropane-1-carboxylate.

The novel process of the invention for the preparation of compounds of formula I comprises reacting 2,2-dimethyl-3-formyl-cyclopropane-1-carboxylic acid in its trans form of the formula

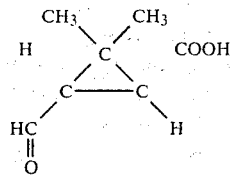

or the cis lactone of 2,2-dimethyl-3-dihydroxymethyl-cyclopropane-1-carboxylic acids of the formula

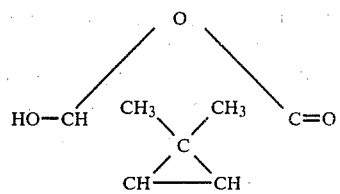

in their racemic or optically active form with a deshydrating agent selected from the group consisting of dicyclohexyl carbodiimide and diisopropyl carbodiimide in a non-polar organic solvent in the presence of pyridine or 4-dimethylamino-pyridine to obtain respectively (cyclohexylamino) (cyclohexylimino) methyl 2,2-dimethyl-3-formyl-cyclopropane-1-carboxylate or (isopropylamino) (isopropylimino)methyl 2,2-dimethyl-3-formylcyclopropane-1-carboxylate with the acid moiety having racemic or optically active, trans or cis structure, reacting one of the latter with (RS)α-cyano-3-phenoxy-benzyl alcohol in a non-polar solvent to obtain (RS)α-cyano-3-phenoxy-benzyl 2,2-dimethyl-3-formyl-cyclopropane-1-carboxylate in racemic or optically active, cis or trans structure having the formula

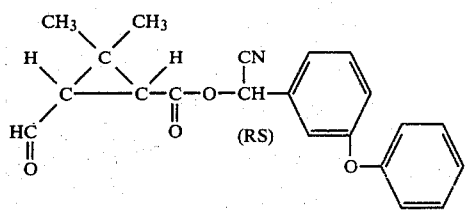

reacting the latter in a non-polar organic solvent with a primary amine of the formula Z-NH$_2$ to obtain (RS)α-cyano-3-phenoxy-benzyl 2,2-dimethyl-3-(Z-iminomethyl)-cyclopropane-1-carboxylate (formula I$_A$) and, if desired, reacting the latter with a basic agent in a solvent or mixture of solvents in which the ester of the alcohol of the (S) or (R) configuration is more soluble than its diastereoisomer to permit after epimerization of the asymmetric carbon of the alcohol moiety to obtain in a crystalline form only the ester corresponding to the configuration favoured by its insolubility which is either (S)α-cyano-3-phenoxy-benzyl 2,2-dimethyl-3-(Z-iminomethyl)-cyclopropane-1-carboxylate or (R)α-cyano-3-phenoxy-benzyl 2,2-dimethyl-3-(Z-iminomethyl)-cyclopropane-1-carboxylate with the acid moiety having the starting configuration.

The non-polar organic solvent used in both of the above steps is preferably selected from the group consisting of aromatic hydrocarbons, aliphatic hydrocarbons, halogenated aliphatic hydrocarbons and cyclohexane. The primary amine is selected from the above group but is preferably aniline.

The basic agent for reaction with the ester of formula $I_4$ is preferably selected from the group consisting of ammonia, triethylamine, diethylamine, morpholine, pyrrolidine, piperidine, diisopropylamine, ephedrine, triethylenediamine, benzylamine, n-butylamine, sec-butylamine, tetrabutyl ammonium hydroxide, strongly basic ion exchange resins containing amine or quaternary ammonium groups and high molecular weight amines and catalytic amounts of strong bases selected from the group consisting of sodium hydroxide, potassium hydroxide, alkali metal hydrides, alkali metal amides, alkali metal alcoholates such as potassium tert.-butylate and sodium isopropylate. The solvent or mixture of solvents used for the basic treatment is preferably selected from the group consisting of acetonitrile, lower alkanols and mixtures of lower alkanols and petroleum ether.

Without limiting the scope of the invention, the following theoretical explanation is given for the transformation of the (RS) ester of formula $I_4$ into the ester of the alcohol of the (S) configuration or of the (R) configuration. All or part of the (R) or (S) form present in the (RS) ester of formula $I_4$ is insolubilized by the action of the insolubilizing solvent or mixture of solvents used and the basic agent racemizes the remainder of the ester of the (R) or (S) alcohol to form again more (RS) ester of formula $I_4$. The mechanism then proceeds with another selective insolubilization of one of the (R) and (S) forms, racemization, etc.

Another process of the invention is for the preparation of all stereoisomeric forms of a compound of the formula

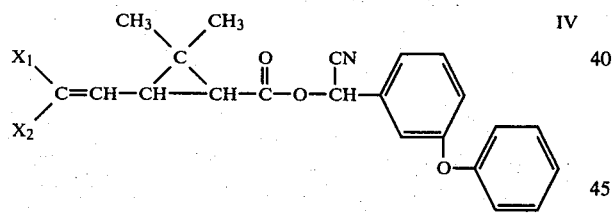

wherein $X_1$ and $X_2$ are individually selected from the group consisting of alkyl of 1 to 4 carbon atoms, fluorine, chlorine and bromine or taken together with the carbon atom to which they are attached from a carbon homocycle of 3 to 7 carbon atoms or a heterocycle of the formula

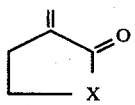

and X is selected from the group consisting of oxygen and sulfur with the acid moiety having the racemic or optically active, cis or trans structure and the alcohol moiety having the (R) or (S) configuration comprising reacting an ester of formula I with the alcohol moiety having the (S) or the (R) configuration with an acid hydrolysis agent to obtain a compound of the formula

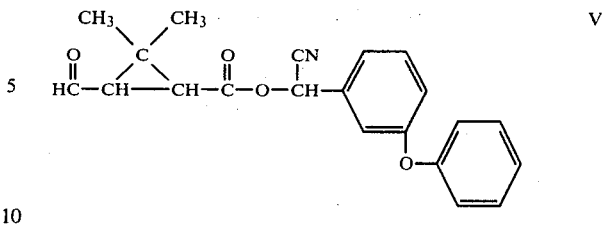

with the same configuration of the starting ester, reacting the latter in an organic solvent with a phosphorane of the formula

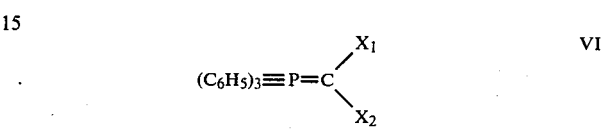

resulting from the reaction of a strong base with a compound of the formula

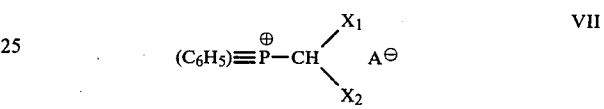

wherein $X_1$ and $X_2$ are halogen and $A^\ominus$ is a mineral acid anion resulting from the reaction of triphenylphosphine and a haloform with a strong base in an organic solvent Y to obtain the compound of formula IV with the same configuration of the starting ester.

In a preferred embodiment of the latter process, the acid hydrolysis agent is selected from the group consisting of sulfuric acid, hydrochloric acid, phosphoric acid and p-toluene sulfonic acid and the hydrolysis is effected in a water-miscible organic solvent. The strong base is selected from the group consisting of alkali metal hydrides, alkali metal amides, alkali metal alcoholates and butyllithium. The solvent Y is selected from the group consisting of dimethylformamide, dimethylsulfoxide, tetrahydrofuran, ether, monoethyl ether of diethyleneglycol and the diethyl ether of diethyleneglycol.

To effect the Wittig reaction which permits the fixing of the 3-lateral side chain of the ester IV, the phosphorane VI is prepared by reacting the strong base with a phosphonium salt or a mixture of triphenylphosphine and a haloform in a polar solvent Y. The ylide formed is then reacted in the presence of an excess of base with the aldehyde compound of formula V. To ensure that the Wittig reaction takes place, the order of the introduction of the reactants may be slightly modified, for example by introducing the base last and realizing as well, simultaneously, the phosphorane formation and its condensation with the aldehyde of compound V.

In summary, the process of the preparation of the compounds of formula I and their use permits one to begin from the trans form of 2,2-dimethyl-3-formyl-cyclopropane-1-carboxylic acid of formula $II_1$, or the cis lactone of 2,2-dimethyl-3-dihydroxymethyl-cyclopropane-1-carboxylic acid of formula $II_2$ and (RS)α-cyano-3-phenoxy-benzyl alcohol to obtain in 5 steps, the esters of cyclopropane-carboxylic acids with the alcohol moiety in the (R) or (S) configuration with various side chains in the 3-position which are well known to have a great insecticidal activity.

The synthesis of the compounds of formula I may be effected on an industrial scale and it is possible to effect the various reaction steps without purification or isolation of the various intermediates. The reactants of the synthesis are common and without danger.

The preparation of the compounds of formula III starting from the trans form of 2,2-dimethyl-3-formyl-cyclopropane-1-carboxylic acid or the cis lactone of 2,2-dimethyl-3-dihydroxymethyl-cyclopropane-1-carboxylic acid and the said alcohol has an original character as the esterification of the aldehyde of formula II with (RS)α-cyano-3-phenoxy-benzyl alcohol leads to a condensation of the alcohol with the aldehyde group and not with the acid group. The passage through (cyclohexylamino)(cyclohexylimino)methyl 2,2-dimethyl-3-formyl-cyclopropane-1-carboxylate as intermediate permits a normal esterification with (RS)α-cyano-3-phenoxy-benzyl alcohol leading to the desired compound of formula III. The classical methods of preparation of compounds of formula III require ozonolysis of a (RS)α-cyano-3-phenoxy-benzyl chrysanthemate which presents a less desirable industrial character as compared to the present process.

The synthesis of compounds of formula I leads without risk of failure to the desired compounds of formula IV whatever side chain at position 3 this ester possesses. In effect, the epimerization process is effected in the process of the invention with compounds containing an imino group and gives a satisfactory yield in this step. The synthesis of the invention is free of all hazards and proceeds practically certainly to obtain the compound of formula IV of determined stereochemistry and a determined structure for the 3-lateral side chain so that one can very precisely obtain a group of compounds with a considerably varied biological activity with a steric structure.

The novel intermediate products of the invention are all the stereoisomeric forms of (cyclohexylamino)(cyclohexylamino)methyl 2,2-dimethyl-3-formyl-cyclopropane-1-carboxylate, (isopropylamino)(isopropylimino)methyl 2,2-dimethyl-3-formyl-cyclopropane-1-carboxylate, (RS)α-cyano-3-phenoxy-benzyl 2,2-dimethyl-3-formyl-cyclopropane-1-carboxylate and (S)α-cyano-3-phenoxy-benzyl 2,2-dimethyl-3-formyl-cyclopropane-1-carboxylate.

In the following examples there are described several preferred embodiments to illustrate the invention. However, it should be understood that the invention is not intended to be limited to the specific embodiments.

EXAMPLE 1

(S)α-cyano-3-phenoxy-benzyl 1R, cis 2,2-dimethyl-3-(2,2-dichlorovinyl)-cyclopropane-1-carboxylate STEP A: (cyclohexylamino) (cyclohexylimino)methyl 1R, cis 2,2-dimethyl-3-formyl-cyclopropane-1-carboxylate 2 ml of pyridine and 28.2 g of the lactone of cis 2,2-dimethyl-3S-(dihydroxymethyl)-cyclopropane-1R-carboxylic acid were added to 400 ml of methylene chloride and then 41.2g of dicyclohexylcarbodiimide were added thereto. The mixture was stirred at 20° C. for one hour to obtain a solution containing (cyclohexylamino)(cyclohexylimino)methyl 1R, cis 2,2-dimethyl-3-formyl-cyclopropane-1-carboxylate which was used for the next step.

STEP B: (R,S)α-cyano-3-phenoxy-benzyl 1R, cis 2,2-dimethyl-3-formyl-cyclopropane-1-carboxylate A solution of 28 g of (R,S)α-cyano-3-phenoxy-benzyl alcohol in 150 ml of methylene chloride was added to the solution of Step A and the mixture was stirred at 20° C. for 16 hours and was filtered. The organic filtrate was washed with water, aqueous 2 N hydrochloric acid and then with water, was dried and evaporated to dryness under reduced pressure. The residue was taken up in ether and the mixture was filtered. The filtrate was evaporated to dryness to obtain 59.1 g of raw (R,S)α-cyano-3-phenoxy-benzyl 1R, cis 2,2-dimethyl-3-formyl-cyclopropane-1-carboxylate which was used as is for the next step.

STEP C: (R,S)α-cyano-3-phenoxyl-benzyl 1R, cis 2,2-dimethyl -3-(phenyliminomethyl)-cyclopropane-1-carboxylate A mixture of 59.1 g of the product of Step B, 12.5 ml of aniline and 400 ml of benzene was refluxed for 3½ hours while azeotropically distilling off the water of reaction formed and was then evaporated to dryness to obtain 77 g of raw (R,S)α-cyano-3-phenoxy-benzyl 1R, cis 2,2-dimethyl -3-(phenyliminomethyl)-cyclopropane-1-carboxylate which was used as is for the next step.

STEP D: (S)α-cyano-3-phenoxy-benzyl 1 R, cis 2,2-dimethyl-3-(phenyliminomethyl)-cyclopropane-1-carboxylate The product of Step C was added to a mixture of 300 ml of isopropanol and 5 ml of triethylamine and crystallization was started. The mixture was stirred at 20° C. for 80 hours and was then cooled to 0° C. and vacuum filtered. The recovered crystals were dried to obtain 17 g of (S)α-cyano-3-phenoxy-benzyl 1R, cis 2,2-dimethyl-3-(phenyliminomethyl)- cyclopropane-1-carboxylate melting at 116° C.

STEP E: (S)α-cyano-3-phenoxy-benzyl 1R, cis 2,2-dimethyl-3-formyl-cyclopropane-1-carboxylate A mixture of 5 g of the product of Step D and 100 ml of aqueous 2 N hydrochloric acid was stirred at 20° C. for 4½ hours and was then extracted with methylene chloride. The organic phase was washed with water and evaporated to dryness under reduced pressure. The residue was chromatographed over silica gel and was eluted with benzene to obtain 3.8 g of (S)α-cyano-3-phenoxy-benzyl 1R, cis 2,2-dimethyl-3-formyl-cyclopropane-1-carboxylate melting at 104° C.

NMR Spectrum (deuterochloroform)

Peaks at 1.25–1.43 ppm (hydrogens of geminal methyls); at 1.8–2.25 ppm (1- and 3-hydrogens of cyclopropyl); at 6.4 ppm (hydrogen on carbon attached to —CN); at 6.91–7.6 ppm (hydrogens of aromatic ring); at 9.8–9.9 ppm (formyl hydrogen).

STEP F: ( S)α-cyano-3-phenoxy-benzyl 1R, cis 2,2-dimethyl-3-(2,2-dichlorovinyl)-cyclopropane-1-carboxylate 1.8 g of chloroform were added at −10° C. to a mixture of 3.93 g of ground triphenylphosphine, 1.12 g of tert.-butanol, 1.7 g of potassium tert.-butylate and 25 ml of heptane and the mixture was stirred at +10° C. for one hour. A solution of 3.49 g of the product of Step E in 20 ml of tetrahydrofuran was added to the mixture which was then stirred at 10° C. for 3 hours and was filtered. 100 ml of an aqueous saturated monosodium phosphate solution were added to the filtrate and the mixture was allowed to stand at rest. The decanted organic phase was evaporated to dryness under reduced pressure and the residue was chromatographed over silica gel. Elution with a 4-6 benzene-cyclohexane mixture yielded 3.4 g of (S)α-cyano-3-phenoxy-benzyl 1R, cis 2,2-dimethyl-3-(2,2-dichlorovinyl)-cyclopropane-1-carboxylate melting at 60° C.

NMR Spectrum (deuterochloroform)

Peaks at 1.18-1.23 ppm (hydrogens of geminal methyls); at 1.8-1.93 ppm and 2.0-2.15-2.30 ppm (1- and 3-hydrogens of cyclopropyl); at 6.10-6.20 ppm (ethylenic hydrogen); at 6.33 ppm (hydrogen on carbon attached to —CN); at 6.83-7.50 ppm (hydrogens of aromatic ring).

EXAMPLE 2

(S)α-cyano-3-phenoxy-benzyl 1R, trans 2,2-dimethyl-3-(2,2-dichlorovinyl)-cyclopropane-1-carboxylate STEP A: (cyclohexylamino)(cyclohexylimino)methyl 1R, trans 2,2-dimethyl-3-formyl-cyclopropane-1-carboxylate 41.2 g of dicyclohexyl carbodiimide were added to a mixture of 300 ml of methylene chloride, 2 ml of pyridine and 28.4 g of 1R, trans 2,2-dimethyl-3-formyl-cyclopropane-1-carboxylic acid and the mixture was stirred at 20° C. for one hour to obtain a suspension containing (cyclohexylamino)(cyclohexylimino)methyl 1R, trans 2,2-dimethyl-3-formyl-cyclopropane-1-carboxylate.

STEP B: (RS)α-cyano-3-phenoxy-benzyl 1R, trans 2,2-dimethyl-3-formyl-cyclopropane-1-carboxylate 30 g of (R,S)α-cyano-3-phenoxy-benzyl alcohol were added to the suspension of Step A and the mixture was stirred at 20° C. for 16 hours and was then filtered. The filtrate was evaporated to dryness under reduced pressure and the residue was chromatographed over silica gel. Elution with a 95-5 benzene-ethyl acetate mixture yielded 38 g of (RS)α-cyano-3-phenoxy-benzyl 1R, trans 2,2-dimethyl-3-formyl-cyclopropane-1-carboxylate.

NMR Spectrum (deuterochloroform)

Peaks at 1.27-1.29-1.30-1.36 ppm (hydrogens of geminal methyls); at 2.16-2.50 ppm (1- and 3-hydrogens of cyclopropyl); at 6.30 ppm (hydrogen on carbon attached to —CN); at 6.83-7.60 ppm (hydrogens of aromatic ring).

STEP C: (R,S)α-cyano-3-phenoxy-benzyl 1R, trans 2,2-dimethyl-3-(phenyliminomethyl)-cyclopropane-1-carboxylate A mixture of 4 g of aniline, 10 g of the product of Step B and 100 Ml of petroleum ether (b.p.=35-70° C.) was refluxed while azeotropically distilling the water of reaction formed and was then evaporated to dryness under reduced pressure to obtain 14.4 g of raw (R,S)α-cyano-3-phenoxy-benzyl 1R, trans 2,2-dimethyl-3-(phenyliminomethyl)-cyclopropane-1-carboxylate which was used as is for the next step.

STEP D: (S)α-cyano-3-phenoxy-benzyl 1R, trans 2,2-dimethyl-3-(phenyliminomethyl)-cyclopropane-1-carboxylate 14.4 g of the product of Step C were added to 40 ml of isopropanol and crystallization was started. The mixture was stirred at 20° C. for 96 hours and was cooled to −10° C. and vacuum filtered. The recovered product was dried to obtain 8.7 g of (S)α-cyano-3-phenoxy-benzyl 1R, trans 2,2-dimethyl-3-(phenyliminomethyl)-cyclopropane-1-carboxylate melting at 94° C.

NMR Spectrum (deuterochloroform)

Peaks at 1.32 ppm (hydrogens of geminal methyls); at 2.30-2.65 ppm (1- and 3-hydrogens of cyclopropyl); at 6.40 ppm (hydrogen on carbon attached to —CN); 7.66-7.76 ppm (ethylenic hydrogen).

IR Spectrum (chloroform)

Absorption at 1740 cm$^{-1}$ (ester carbonyl); at 1640 cm$^{-1}$ (conjugated —CN); at 1497 and 1487 cm$^{-1}$ (aromatic ring); at 1382 cm$^{-1}$ (geminal methyls); at 692 cm$^{-1}$ (phenyl).

STEP E: (S)α-cyano-3-phenoxy-benzyl 1R, trans 2,2-dimethyl-3-formyl-cyclopropane-1-carboxylate A mixture of 5 g of the product of Step D in 100 ml of aqueous 2 N hydrochloric acid was stirred at 20° C. for 2½ hours and was then vacuum filtered. The recovered product was dissolved in methylene chloride and the solution was dried and evaporated to dryness under reduced pressure to obtain 4.2 g of (S)α-cyano-3-phenoxy-benzyl 1R, trans 2,2-dimethyl-3-formyl-cyclopropane-1-carboxylate melting at 70° C.

NMR Spectrum (deuterochloroform)

Peaks at 1.26-1.29 ppm (hydrogens of geminal methyls); at 2.53 ppm (1- and 3-hydrogen of cyclopropane); at 6.4 ppm (hydrogen on carbon attached to —CN); at 6.90-7.50 ppm (hydrogens of aromatic ring); at 9.76-9.80 ppm (hydrogen of formyl).

STEP F: (S)α-cyano-3-phenoxy-benzyl 1R, trans 2,2-dimethyl-3-(2,2-dichlorovinyl)-cyclopropane-1-carboxylate A mixture of 3.93 g of triphenyl phosphine, 1.12 g of tert.-butanol, 1.7 g of potassium tert.-butylate and 25 ml of heptane was cooled to −10° C. and 1.8 g of chloroform were added thereto. The mixture was stirred at 15° C. for one hour and was then cooled to −20° C. A solution of 3.5 g of the product of Step E in 10 ml of tetrahydrofuran was added to the mixture which was then stirred for 2½ hours at −10° C. The mixture was poured into an aqueous monsodium phosphate solution and was extracted with ether. The organic extract was evaporated to dryness under reduced pressure and the residue was chromatographed over silica gel. Elution with benzene yielded 3.4 g of (S)α-cyano-3-phenoxy-benzyl 1R, trans 2,2-dimethyl-3-(2,2-dichlorovinyl)-cyclopropane-1-carboxylate.

NMR Spectrum (deuterochloroform)

Peaks at 1.18-1.24 ppm (hydrogens of geminal methyls); at 1.60-1.70 ppm (1-hydrogen of cyclopropyl); at 2.20-2.29-2.30-2.40 ppm (3-hydrogen of cyclopropyl); at 5.58-5.70 ppm (ethylenic hydrogen); at 6.43 ppm (hydrogen on carbon attached to —CN); at 6.9-7.60 ppm (hydrogens of aromatic ring).

EXAMPLE 3

(S)α-cyano-3-phenoxy-benzyl 1R, trans 2,2-dimethyl-3-[(E+Z)-2-chloro-2-bromo-ethenyl]-cyclopropane-1-carboxylate A mixture of 25 g of ground triphenyl phosphine, 9 g of potassium tert.-butylate, 6 g of tert.-butanol and 130 ml of heptane was stirred at room temperature for 30 minutes and then a solution of 17 g of chlorodibromomethane in 40 ml of heptane was added thereto at 0° C. The mixture was stirred at 0° to 5° C. for 45 minutes and then a solution of 17.6 g of (S)α-cyano-3-phenoxy-benzyl 1R, trans 2,2-dimethyl-3-formyl-cyclopropane-1-carboxylate in 80 ml of tetrahydrofuran was added thereto at 0° C. The mixture was stirred at 5° C. for 30 minutes and was then poured into an aqueous N sulfuric acid solution. The mixture was extracted with ethyl acetate and the organic phase was washed with water and evaporated to dryness under reduced pressure. The residue was chromatographed over silica gel and was eluted with a 7-3 benzene-cyclohexane mixture to obtain 16.5 g of (S)α-cyano-3-phenoxy-benzyl 1R, trans 2,2dimethyl-3-[(E+Z)-2-chloro-2-bromo-ethenyl]-cyclopropane-1-carboxylate with a specific rotation of $[\alpha]_D^{20} = +31°$ (c=0.6% in benzene).

IR Spectrum (chloroform);

Absorption at 1738 cm$^{-1}$ (ester carbonyl); at 1585 and 1485 cm$^{-1}$ (aromatic ring); at 1351 and 1381 cm$^{-1}$ (geminal methyls).

NMR Spectrum (deuterochloroform)

Peaks at 1.16–1.20 ppm (hydrogens of geminal methyls); at 1.62–1.70 ppm (1-hydrogen of cyclopropane); at 5.77–5.90–5.80–5.95 ppm (ethylenic hydrogen); at 6.38 ppm (hydrogen of carbon attached to —CN); at 6.91–7.50 ppm (hydrogens of aromatic ring).

Various modifications of the compounds and process of the invention may be made without departing from the spirit or scope thereof and it is to be understood that the invention is intended to be limited only as defined in the appended claims.

We claim:

1. An imino derivative of esters of 3-formyl-cyclopropane-1-carboxylic acids in their various isomeric forms and mixtures thereof of the formula

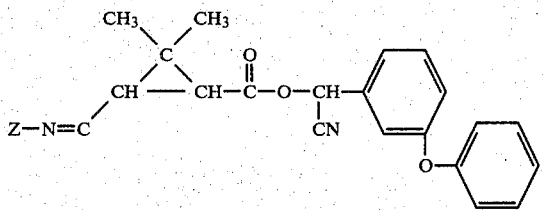

wherein Z is an organic residue of a primary amine of the formula Z-NH$_2$ and the acid moiety may have the cis or trans configuration and the alcohol moiety may have the R,S or RS configuration.

2. A compound of claim 1 which is (RS)α-cyano-3-phenoxy-benzyl 1R, cis 2,2-dimethyl-3-(phenyliminomethyl)-cyclopropane-1-carboxylate.

3. A compound of claim 1 which is (S)α-cyano-3-phenoxy-benzyl 1R, cis 2,2-dimethyl-3-(phenyliminomethyl)-cyclopropane-1-carboxylate.

4. A compound of claim 1 which is (RS)α-cyano-3-phenoxy-benzyl 1R, trans 2,2-dimethyl-3-(phenyliminomethyl)-cyclopropane-1-carboxylate.

5. A compound of claim 1 which is (S)α-cyano-3-phenoxy-benzyl 1R, trans 2,2-dimethyl-3-(phenyliminomethyl)-cyclopropane-1-carboxylate.

6. A process for the preparation of a compound of claim 1 comprising reacting 2,2-dimethyl-3-formyl-cyclopropane-1-carboxylic acid in its trans form of the formula

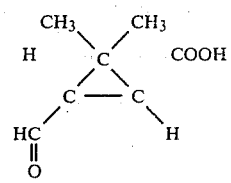

or the cis lactone of 2,2-dimethyl-3-dihydroxymethyl-cyclopropane-1-carboxylic acids of the formula

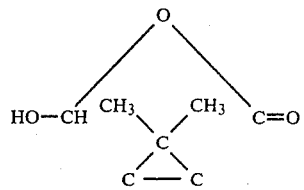

in their racemic or optically active form with a deshydrating agent selected from the group consisting of dicyclohexyl carbodiimide and diisopropyl carbodiimide in a non-polar organic solvent in the presence of pyridine or 4-dimethylamino-pyridine to obtain respectively (cyclohexylamino)(cyclohexylimino)methyl 2,2-dimethyl-3-formyl-cyclopropane-1-carboxylate or (isopropylamino)(isopropylimino)methyl 2,2-dimethyl-3-formylcyclopropane-1-carboxylate with the acid moiety having racemic or optically active, trans or cis structure, reacting one of the latter with (RS)α-cyano-3-phenoxy-benzyl alcohol in a non-polar solvent to obtain (RS)α-cyano-3-phenoxy-benzyl 2,2-dimethyl-3-formyl-cyclopropane-1-carboxylate in racemic or optically active, cis or trans structure having the formula

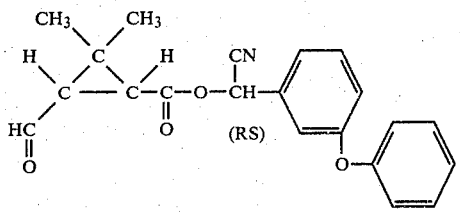

reacting the latter in a non-polar organic solvent with a primary amine of the formula Z-NH$_2$ to obtain (RS)α-cyano-3-phenoxy-benzyl 2,2-dimethyl-3-(Z-iminomethyl)-cyclopropane-1-carboxylate (formula I$_4$) and, if desired, reacting the latter with a basic agent in a solvent or mixture of solvents in which the ester of the alcohol of the (S) or (R) configuration is more soluble than its diastereoisomer to permit after epimerization of the asymetric carbon of the alcohol moiety to obtain in a crystalline form only the ester corresponding to the configuration favoured by its insolubility which is either (S)α-cyano-3-phenoxy-benzyl 2,2-dimethyl-3-(Z- iminomethyl)-cyclopropane-1-carboxylate or (R)α-cyano-3-phenoxy-benzyl 2,2-dimethyl-3-(Z-iminomethyl)-cyclopropane-1-carboxylate with the acid moiety having the starting configuration.

7. The process of claim 6 wherein the non-polar organic solvents are selected from the group consisting of aromatic hydrocarbons, aliphatic hydrocarbons, halogenated aromatic hydrocarbons and cyclohexane.

8. The process of claim 6 wherein the primary amine is aniline.

9. The process of claim 6 wherein the basic agent is selected from the group consisting of ammonia, triethylamine, diethylamine, morpholine, pyrrolidine, piperidine, diisopropylamine, ephedrine, triethylenediamine, benzylamine, n-butyamine, sec-butylamine, tetrabutyl ammonium hydroxide, strongly basic ion exchange resins containing amine or quaternary ammonium groups and high molecular weight amines and catalytic amounts of strong bases selected from the group consisting of sodium hydroxide, potassium hydroxide, alkali metal amides, alkali metal hydrides, alkali metal alcoholates.

10. The process of claim 9 wherein the solvent is selected from the group consisting of acetonitrile, lower alkanols and mixtures of lower alkanols and petroleum ether.

* * * * *

UNITED STATES PATENT AND TRADEMARK OFFICE
CERTIFICATE OF CORRECTION

PATENT NO. : 4,312,817
DATED : January 26, 1982          Page 1 of 2
INVENTOR(S) : JACQUES MARTEL ET AL.

It is certified that error appears in the above—identified patent and that said Letters Patent is hereby corrected as shown below:

Title page [30]: "France    79 390843" should read
                 -- France    79 30843 --.

Column 2, Formula $II_1$, and Column 10, lines 12-18: That formula should read:

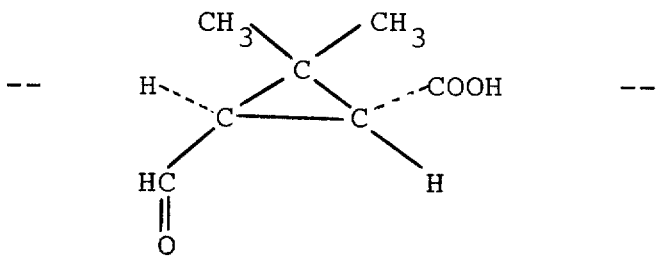

Column 2, Formula $II_2$, and Column 10, lines 23-30: That formula should read

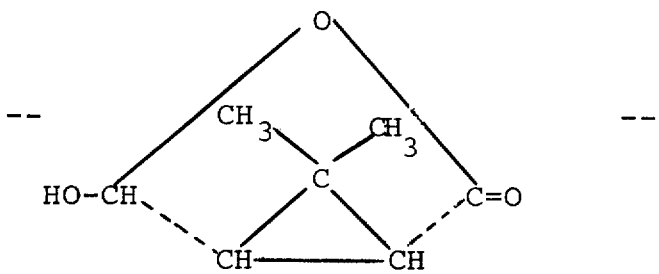

UNITED STATES PATENT AND TRADEMARK OFFICE
CERTIFICATE OF CORRECTION

PATENT NO. : 4,312,817
DATED : January 26, 1982
INVENTOR(S) : JACQUES MARTEL ET AL.

It is certified that error appears in the above—identified patent and that said Letters Patent is hereby corrected as shown below:

Column 7, line 62: "100 Ml" should read -- 100 ml --.

Column 9, line 24: "2,2dimethyl" should read -- 2,2-dimethyl --

Column 11, lines 9/10: "amineis" should read -- amine is --.

Signed and Sealed this

Twenty-fifth Day of May 1982

[SEAL]

Attest:

GERALD J. MOSSINGHOFF

*Attesting Officer*  *Commissioner of Patents and Trademarks*